(12) United States Patent
Colleran

(10) Patent No.: US 6,206,928 B1
(45) Date of Patent: Mar. 27, 2001

(54) ORTHOPAEDIC TRAY TRIAL

(75) Inventor: Dennis P. Colleran, Plainville, MA (US)

(73) Assignee: Depuy Orthpaedics, Inc., Warsaw, IN (US)

( * ) Notice: Subject to any disclaimer, the term of this patent is extended or adjusted under 35 U.S.C. 154(b) by 0 days.

(21) Appl. No.: 09/302,708

(22) Filed: Apr. 29, 1999

(51) Int. Cl.⁷ .................................................... A61F 2/38
(52) U.S. Cl. ............................................................ 623/20.3
(58) Field of Search ....................... 606/86, 88; 623/20.3, 623/20.32

(56) References Cited

U.S. PATENT DOCUMENTS

| | | | | |
|---|---|---|---|---|
| 4,919,671 | * | 4/1990 | Karpf | 623/20.3 |
| 5,766,256 | * | 6/1998 | Oudard et al. | 623/20.32 |
| 5,976,147 | * | 11/1999 | Lasalle | 606/88 |

* cited by examiner

*Primary Examiner*—David J. Isabella
(74) *Attorney, Agent, or Firm*—Nutter, McClennen & Fish, LLP

(57) ABSTRACT

An orthopaedic tray trial includes a base plate and at least one movable fastening member attached to the base plate. The fastening member includes a striking element and a bone penetrating pin extending from the striking element. The fastening element may be rotatably attached to the base plate using a hinge pin to connect the striking element to the base plate.

15 Claims, 2 Drawing Sheets

ORTHOPAEDIC TRAY TRIAL

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to an orthopaedic tray trial having at least one attached fastening element.

BACKGROUND OF THE INVENTION

During knee replacement surgery tibial trials are used to assist a surgeon in preparing the tibial surface for implantation of the tibial portion of the artificial knee. A surgeon uses a tibial tray trial to determine the tibial implant size, to make the appropriate cuts and reams in the bone, and to ensure a proper alignment and tibial component thickness prior to implanting the tibial components.

Such a procedure typically entails making an initial tibial plateau cut on the proximal tibial portion of the knee; determining a preferred size tray trial (and ultimately tray implants); placing the selected tray trial over the tibial surface; performing a trial reduction to ensure proper tibial component thickness and alignment; attaching a punch guide to the tibial tray trial; and cutting or reaming the tibial bone through openings in the punch guide and tray trial to prepare it to receive a stem or keel of the tibial implant. During this procedure it is necessary to fix the tray trial to the tibia, at least before cutting or reaming the tibial bone through openings in the punch guide and tray trial.

Known tibial tray trials, as illustrated in FIG. 1, typically include a tibial alignment handle 10 is attached to the tibial tray trial 12 to properly locate the trial with respect to a prepared tibia 14. Pins 16 are then driven through holes in the tray trial to fix the tray trial to the tibia 14. At least three hands are require to fix tibial tray trial 12 to tibia 14: one hand holds the tray trial 12 in place using handle 10; a second holds a pin 16 in place; and a third hand drives pin 14 through tray trial 12 into tibia 14 to fix the tray trial 12 thereto.

One difficulty with the known method for fixing a tibial tray trial to a tibia is that, because it requires more than two hands, a surgeon cannot fix the tray trial without help. Another problem involves the pins themselves. Because the pins must be removed in order to remove the trial to place the permanent prosthesis, they typically include portions that extend above the tray trial to facilitate their removal. However, trialing sometimes involves, particularly when implanting a rotating platform knee tibial prosthesis, moving or rotating a trial insert with respect to the tibial tray trial. When the pins extend above the surface of the tibial tray trial, the pins can prevent relative movement between the tray trial and the trial insert. In addition, pins that are separate from the tray may become lost during surgery, cleaning, or transportation.

SUMMARY OF THE INVENTION

The present invention provides an orthopaedic tray trial for attachment to a resected bone surface having a base plate and at least one movable fastening element attached to the base plate. The base plate has a bone contacting surface and an opposed working surface. The fastening element includes a striking element and a bone penetrating pin attached to the striking element and extending in a direction from the working surface toward the bone contacting surface of the base plate.

The fastening elements may be selectively movable between an open position and a closed position. In the open position, the bone penetrating pin does not extend beyond the bone contacting surface of the base plate, and in the closed position, the striking element does not extend beyond the working surface.

In one embodiment, the fastening element is rotatably attached to the base plate using a hinge pin to connect the striking element to the base plate. The orthopaedic tray trial of the invention may be configured for use as a tibial tray trail for attachment to a resected tibia.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
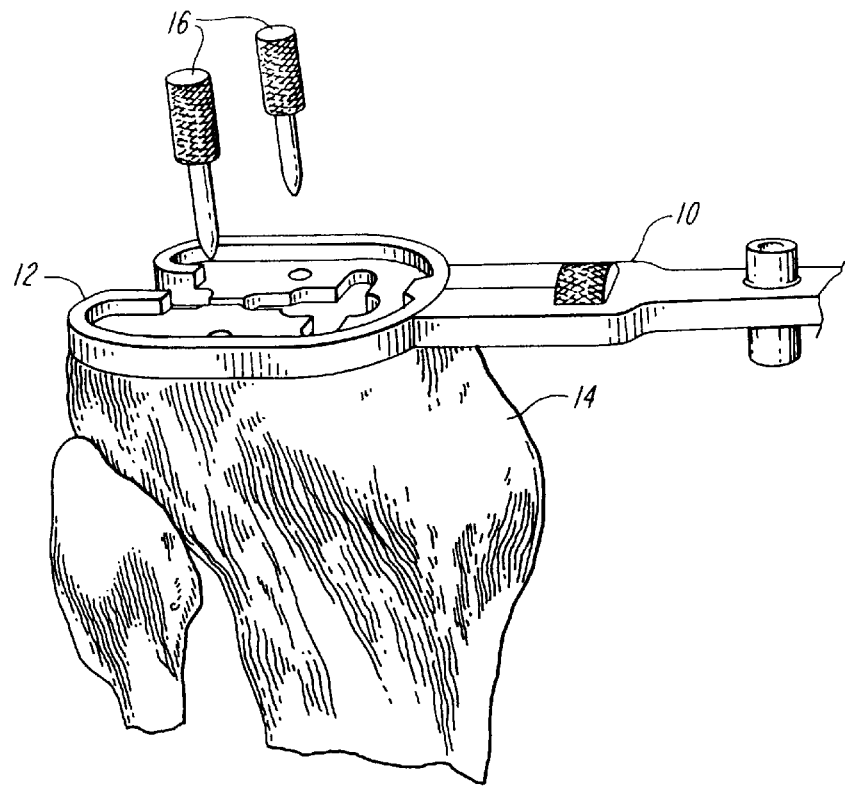
FIG. 1 is a side view of a prior art tibial tray trial fixation system.
Figure 2:
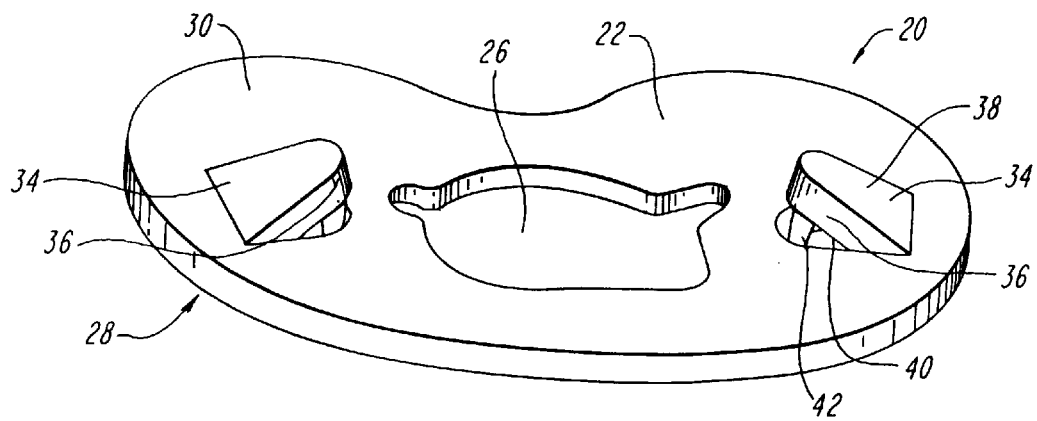
FIG. 2 is a perspective view of an orthopaedic tray trial of the invention in an open position.
Figure 3:
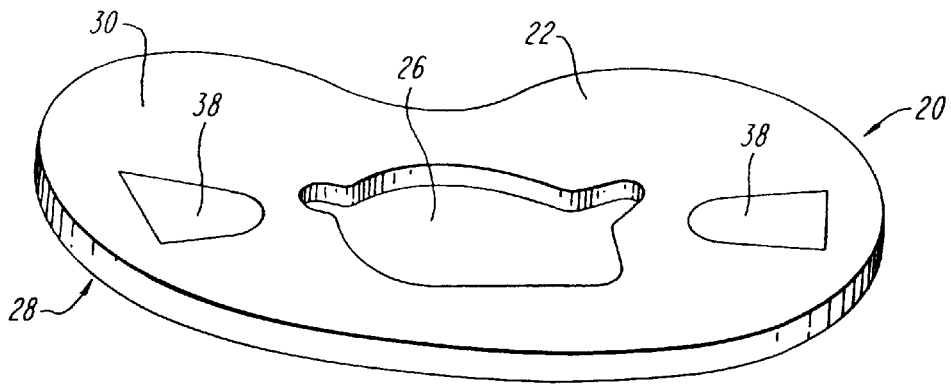
FIG. 3 is a perspective view of the orthopaedic tray trial of FIG. 2 in a closed position.
Figure 4:
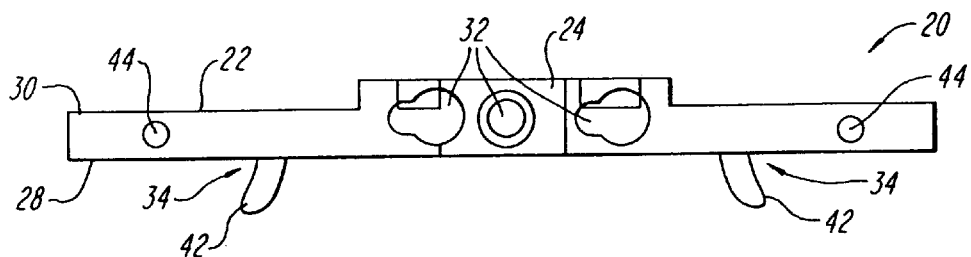
FIG. 4 is a side view of the orthopaedic tray trial of FIG. 2 in a closed position.
Figure 5:
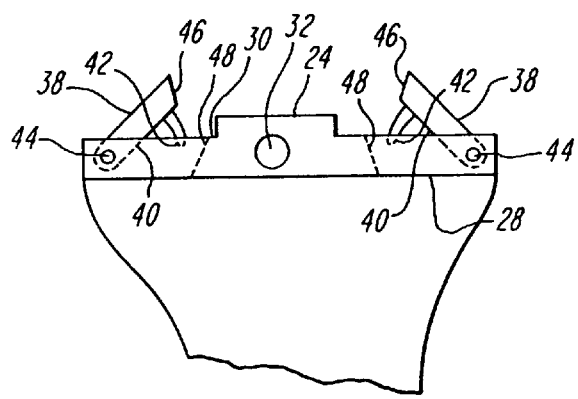
FIG. 5 is a side view of the orthopaedic tray trial of FIG. 2 in an open position set atop a tibia.

Orthopaedic tray trial 20, illustrated in FIGS. 2–5, comprises a plate portion 22, a handle mating portion 24, and a punch guide opening 26 formed in the tray trial plate 22. Orthopaedic tray trial 20 is generally shaped for use as a tibial tray trial and includes an generally flat, inferior bone contacting surface 28 and an opposed superior working surface 30. The mating portion 24 includes holes 32 for receiving bolts of an alignment handle. Tibial tray trial 20 may also include a rim (not shown) around the outer circumference of the plate 22 extending transversely from the working surface 30. A rim may be useful to seat a trial tibial insert. Alternatively, where a rotating platform knee tibial prosthesis will be employed, tibial tray trail 20 typically does not have a circumferential rim.

Tibial tray trial 20 includes two fastening elements 34. More or fewer fastening elements may be employed consistent with the spirit of the invention depending on the particular use of the orthopaedic tray trial of the invention. Each fastening element 34 includes a striking element 36 having a superior surface 38 and an inferior surface 40, and a pin 42 extending from the inferior surface 40 in a general direction from the working surface 30 of base plate 22 toward the bone contacting surface 28.

Fastening elements 34 are rotatably connected to base plate 28 by hinge pins 44. Hinge pins 44 define axes of rotation about which the fastening elements rotate that are coplanar with the base plate 22. The fastening elements 34 rotate between an open position, shown in FIGS. 2 and 5, wherein the striking element 36 is located above the superior surface 30 and no part of the fastening element 34 extends below the bone contacting surface 28 of the base plate 22, and a closed position, shown in FIGS. 3–4, wherein pins 42 extend beyond the bone contacting surface 28 of base plate 22 to fix with a bone and no portion of the fastening element 34 extends above the working surface 30 of base plate 22.

Pins 42 may be curved in a plane transverse to the axis of rotation of the fastening elements 34. This allows pins 42 to enter a bone surface at a perpendicular angle to the surface, and minimizes the amount of bone engaged by pins 42 as they travel into the bone during fixation of the tibial tray trial.

Fastening elements 34 and base plate 22 may also have cooperating surfaces 46, 48, respectively (see FIG. 5), that are angled so as to stop fastening elements 34 in a closed position wherein the superior surface 38 of the fastening elements is substantially flush with the working surface 30 of the base plate 22. This configuration prevents a surgeon from over inserting fastening elements 34 into bone.

In use, the tibial surface is cut so that the tibial tray trial 20 will rest on a flat surface. Tibial tray trial 20 is then used as a template to select the appropriate size tibial prosthesis for implantation. An alignment handle is used to manipulate the tray trial. Various sizes of tray trials are attached and removed from the alignment handle to select a trial closely matching the tibial plateau. The surgeon may do this with one hand leaving the other hand free.

Once the size is selected, the trial is placed to rest on the bone. Holding the handle with one hand, the surgeon can fix the trial to the tibial surface by striking the striking elements 34 with a mallet. Depending on the procedure and the type of tibial prosthesis being implanted, a tibial trial insert (not shown) may be inserted within a rim of tray trial 20. The insert is used to determine the tibial implant thickness and provide a surface with which a femoral trial, indicative of the implant, will interact. Various trial inserts are tried to select the one of an appropriate thickness. Alignment rods may be used to check the alignment of the tray 20 with the femoral portion of the implant. The surgeon may then remove the alignment handle, replace the patella portion and check the alignment and movement of the trials. Once it has been determined that the trial is appropriately sized and fitted and has been appropriately placed on the tibia, the alignment handle and trial insert are removed. The surgeon will also remove the femoral trial and attach a punch guide to the tray trial. In order to prepare the tibia for the tibial implant, a punch or reaming device is then inserted through a punch guide (not shown) which is placed over the punch guide opening 26.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An orthopaedic tray trial for attachment to a resected bone surface comprising:
   a base plate having a bone contacting surface and an opposed working surface; and
   at least one fastening element movably attached to the base plate including:
   a striking element; and
   a bone penetrating pin attached to the striking element and extending in a direction from the working surface to the bone contacting surface.

2. The tray trial of claim 1, further comprising a connecting element having a first end attached to the fastening element and a second end attached to the base plate so as to movably attach the fastening element to the to the base plate.

3. The tray trial of claim 2, wherein the connecting element rotatably connects the striking element to the base plate.

4. The tray trial of claim 3, wherein the connecting element includes a hinge pin rotatable connecting the connecting element to the base plate.

5. The tray trial of claim 3, wherein the striking element rotates about an axis that is coplanar with the base plate and the bone penetrating pin is curved in a plane transverse to the axis of rotation.

6. The tray trial of claim 1, wherein the at least one fastening element is selectively movable between an open position, wherein the penetrating pin does not extend beyond the bone contacting surface, and a closed position wherein the striking element does not extend beyond the working surface.

7. The tray trial of claim 6, wherein the at least one striking element engages the base plate to form a substantially flat surface working surface when the at least one fastening element is in a closed position.

8. A tibial tray trial for attachment to a resected tibia comprising:
   a base plate having a bone contacting surface and an opposed working surface; and
   at least one movable fastening element including:
   a striking element rotatably attached to the base plate, the striking element rotating about an axis of rotation that is coplanar with the base plate; and
   a bone penetrating pin attached to the striking element and extending in a direction from the working surface to the bone contacting surface.

9. The tibial tray trial of claim 8, further comprising a connecting element having a first end attached to the fastening element and a second end attached to the base plate so as to movably attach the fastening element to the to the base plate.

10. The tibial tray trial of claim 9, wherein the connecting element is a hinge pin.

11. The tibial tray trial of claim 8, further comprising an alignment handle removably attached to the base plate.

12. The prosthesis of claim 8, wherein the at least one fastening element is selectively movable between an open position, wherein the penetrating pin does not extend beyond the bone contacting surface, and a closed position wherein the striking element does not extend beyond the working surface.

13. The tray trial of claim 12, wherein the at least one striking element engages the base plate to form a substantially flat surface working surface when the at least one fastening element is in a closed position.

14. The tray trial of claim 8, wherein the base plate includes a circumferential rim for attaching a trial insert.

15. The tray trial of claim 8, wherein the base plate has an opening formed therein to define a punch guide.

* * * * *